(12) United States Patent
Forsgren Brusk et al.

(10) Patent No.: US 9,801,765 B2
(45) Date of Patent: Oct. 31, 2017

(54) ODOUR CONTROL MATERIAL, METHOD FOR PREPARATION OF AN ODOUR CONTROL MATERIAL AND AN ABSORBENT PRODUCT COMPRISING THE ODOUR CONTROL MATERIAL (71) Applicant: SCA Hygiene Products AB, Gothenburg (SE)

(72) Inventors: Ulla Forsgren Brusk, Pixbo (SE); Chatrine Stridfeldt, Hovas (SE); Kent Malmgren, Sundsvall (SE)

(73) Assignee: SCA HYGIENE PRODUCTS AB, Gothenburg (SE)

(*) Notice: Subject to any disclaimer, the term of this patent is extended or adjusted under 35 U.S.C. 154(b) by 336 days.

(21) Appl. No.: 14/441,949

(22) PCT Filed: Nov. 12, 2012

(86) PCT No.: PCT/SE2012/051229
§ 371 (c)(1),
(2) Date: May 11, 2015

(87) PCT Pub. No.: WO2014/074038
PCT Pub. Date: May 15, 2014

(65) Prior Publication Data
US 2015/0290052 A1 Oct. 15, 2015

(51) Int. Cl.
A61L 15/48 (2006.01)
A61F 13/84 (2006.01)
(Continued)

(52) U.S. Cl.
CPC ...... *A61F 13/8405* (2013.01); *A61F 13/1565* (2013.01); *A61F 13/51* (2013.01);
(Continued)

(58) Field of Classification Search
CPC .. A61F 13/1565; A61F 13/51; A61F 13/8405; A61F 2013/5109;
(Continued)

(56) References Cited

U.S. PATENT DOCUMENTS 3,340,875 A 9/1967 Dudley et al.
4,992,326 A 2/1991 Dabi
(Continued)

FOREIGN PATENT DOCUMENTS

CN 101304770 A 11/2008
CN 101325981 A 12/2008
(Continued)

OTHER PUBLICATIONS

Office Action issued on Nov. 25, 2015, by the Chinese Patent Office in corresponding Chinese Patent Application No. 201280076983.6 and an English translation of the Office Action. (7 pages).
(Continued)

*Primary Examiner* — Frank Lawrence
(74) *Attorney, Agent, or Firm* — Buchanan Ingersoll & Rooney P.C.

(57) ABSTRACT

The present invention relates to an odor control material consisting of a water-insoluble particulate odor control agent and a thermoplastic water-soluble carrier matrix encapsulating the odor control agent. The carrier matrix dissolves when in contact with an aqueous solution, such as urine and the odor control material is obtained by means of thermoforming. The invention relates also to a method for the preparation of the odor control material and the use of the odor control material in absorbent products. The present odor control material minimizes dusting problems caused by particulate odor control agents in production processes.

19 Claims, 5 Drawing Sheets (51) Int. Cl.

| | |
|---|---|
| *A61L 15/46* | (2006.01) |
| *A61F 13/15* | (2006.01) |
| *D01F 1/10* | (2006.01) |
| *D01F 6/66* | (2006.01) |
| *A61L 15/18* | (2006.01) |
| *A61F 13/51* | (2006.01) |
| *B01J 20/20* | (2006.01) |
| *B01J 20/22* | (2006.01) |
| *B01J 20/24* | (2006.01) |
| *B01J 20/26* | (2006.01) |
| *B01J 20/28* | (2006.01) |
| *B29C 47/00* | (2006.01) |
| *B29C 47/06* | (2006.01) |
| *D01D 5/08* | (2006.01) |
| *B29K 71/00* | (2006.01) |
| *B29K 507/04* | (2006.01) |

(52) U.S. Cl.
CPC ............... *A61L 15/18* (2013.01); *A61L 15/46* (2013.01); *B01J 20/20* (2013.01); *B01J 20/22* (2013.01); *B01J 20/24* (2013.01); *B01J 20/261* (2013.01); *B01J 20/28004* (2013.01); *B01J 20/28023* (2013.01); *B01J 20/28033* (2013.01); *B29C 47/0066* (2013.01); *B29C 47/06* (2013.01); *D01D 5/08* (2013.01); *D01F 1/10* (2013.01); *D01F 6/66* (2013.01); *A61F 2013/5109* (2013.01); *A61F 2013/842* (2013.01); *A61F 2013/845* (2013.01); *A61F 2013/8408* (2013.01); *A61F 2013/8423* (2013.01); *A61F 2013/8452* (2013.01); *A61L 2300/108* (2013.01); *A61L 2300/62* (2013.01); *B29K 2071/02* (2013.01); *B29K 2507/04* (2013.01); *D10B 2331/06* (2013.01); *D10B 2509/026* (2013.01)

(58) Field of Classification Search
CPC ........ A61F 2013/8408; A61F 2013/842; A61F 2013/8423; A61F 2013/845; A61F 2013/8452; A61L 15/18; A61L 15/46; A61L 2300/108; A61L 2300/62; B29C 47/0066; B29C 47/06; B01J 20/20; B01J 20/22; B01J 20/24; B01J 20/261; B01J 20/28004; B01J 20/28023; B01J 20/28033; B01J 20/28028; B29K 2071/02; B29K 2507/04; D01D 5/08; D01F 1/10; D01F 6/66; D10B 2331/06; D10B 2509/026
USPC .................. 96/108, 154; 422/6, 120, 122
See application file for complete search history.

(56) References Cited

U.S. PATENT DOCUMENTS

| | | | |
|---|---|---|---|
| 5,161,686 A | 11/1992 | Weber et al. | |
| 5,407,442 A | 4/1995 | Karapasha | |
| 6,025,319 A | 2/2000 | Surutzidis et al. | |
| 6,313,371 B1 | 11/2001 | Conant et al. | |
| 6,344,036 B1 | 2/2002 | Ivansson | |
| 6,479,150 B1 | 11/2002 | Liu et al. | |
| 8,168,852 B2 | 5/2012 | Quincy, III | |
| 2004/0018359 A1* | 1/2004 | Haggquist | B01D 53/02 428/402.21 |
| 2004/0121681 A1 | 6/2004 | Lindsay et al. | |
| 2004/0122388 A1 | 6/2004 | McCormack et al. | |
| 2004/0266302 A1* | 12/2004 | DiSalvo | A61L 15/34 442/382 |
| 2006/0142709 A1 | 6/2006 | Quincy, III | |
| 2007/0073255 A1 | 3/2007 | Thomas et al. | |
| 2008/0200890 A1 | 8/2008 | Wood et al. | |
| 2008/0251081 A1* | 10/2008 | Claussen | A41D 13/1115 128/205.27 |
| 2009/0155508 A1* | 6/2009 | Chau | C08J 3/22 428/35.7 |
| 2012/0145008 A1 | 6/2012 | Chau et al. | |
| 2017/0027778 A1 | 2/2017 | Stridfeldt et al. | |
| 2017/0027779 A1 | 2/2017 | Stridfeldt et al. | |

FOREIGN PATENT DOCUMENTS

| | | |
|---|---|---|
| CN | 102046213 A | 5/2011 |
| EP | 0304952 A2 | 3/1989 |
| EP | 0389023 A2 | 9/1990 |
| EP | 0392528 A2 | 10/1990 |
| GB | 2055586 A | 3/1981 |
| JP | S49118299 U | 9/1974 |
| RU | 2 360 406 C1 | 7/2009 |
| WO | 9112029 A1 | 8/1991 |
| WO | 97/01317 A1 | 1/1997 |
| WO | WO 98/01300 A1 | 1/1998 |
| WO | WO 98/41607 A1 | 9/1998 |
| WO | WO 99/39675 A1 | 8/1999 |
| WO | WO 2004/006967 A1 | 1/2004 |
| WO | 2007/067111 A1 | 6/2007 |
| WO | 2007/067112 A1 | 6/2007 |
| WO | 2010/119272 A1 | 10/2010 |
| WO | WO 2012/163995 A1 | 12/2012 |

OTHER PUBLICATIONS

Office Action (Decision of Rejection) issued on Feb. 6, 2017, by the Japanese Patent Office in Japanese Patent pplication No. 2015-541740, and an English Translation of the Office Action. (9 pages).
Notification of Transmittal of the International Preliminary Report on Patentability (Forms PCT/IPEA/416 and PCT/IPEA/409) issued on Dec. 4, 2014, by the European Patent Office in corresponding International Application No. PCT/SE2012/051229. (13 pages).
International Search Report (Form PCT/ISA/210) issued on Sep. 8, 2014, by the European Patent Office in the International Application No. PCT/SE2013/051603. (6 pages).
Written Opinion of the International Searching Authority (Form PCT/ISA/237) issued on Sep. 8, 2014, by the European Patent Office in the International Application No. PCT/SE2013/051603. (9 pages).
Written Opinion of the International Preliminary Examining Authority (Form PCT/IPEA/408) issued Dec. 7, 2015, by the European Patent Office in the International Application No. PCT/SE2013/051603. (7 pages).
International Preliminary Report on Patentability (Form PCT/IPEA/409) issued on Mar. 3, 2016, by the European Patent Office in the International Application No. PCT/SE2013/051603. (12 pages).
International Search Report (Form PCT/ISA/210) issued on Sep. 5, 2014, by the European Patent Office in the International Application No. PCT/SE2013/051602. (6 pages).
Written Opinion of the International Searching Authority (Form PCT/ISA/237) issued on Sep. 5, 2014, by the European Patent Office in the International Application No. PCT/SE2013/051602. (7 pages).
Written Opinion of the International Preliminary Examining Authority (Form PCT/IPEA/408) issued Nov. 25, 2015, by the European Patent Office in the International Application No. PCT/SE2013/051602. (5 pages).
International Preliminary Report on Patentability (Form PCT/IPEA/409) issued on Feb. 9, 2016, by the European Patent Office in the International Application No. PCT/SE2013/051602. (11 pages).
The extended European Search Report issued on Jun. 13, 2016, by the European Patent Office in corresponding European Patent Application No. 12887897.2-1308. (6 pages).
International Search Report (PCT/ISA/210) mailed on Jul. 17, 2013, by the Swedish Patent Office as the International Searching Authority for International Application No. PCT/SE2012/051229.

(56) References Cited

OTHER PUBLICATIONS

Written Opinion (PCT/ISA/237) mailed on Jul. 11, 2013, by the Swedish Patent Office as the International Searching Authority for International Application No. PCT/SE2012/051229.

Office Action issued on Feb. 17, 2017, by the Russian Patent Office in corresponding Russian Patent Application No. 2015122649/15(035409) and an English Translation of the Office Action. (10 pages).

Office Action issued on Mar. 28, 2017, by the Colombia Patent Office in corresponding Colombian Patent Application No. 15134574. (11 pages).

Office Action dated Jul. 6, 2017, by the Russian Patent Office in corresponding Russian Patent Application No. 2015122649/15(035409) and an English Translation of the Office Action. (11 pages).

\* cited by examiner

ODOUR CONTROL MATERIAL, METHOD FOR PREPARATION OF AN ODOUR CONTROL MATERIAL AND AN ABSORBENT PRODUCT COMPRISING THE ODOUR CONTROL MATERIAL

TECHNICAL FIELD

The present invention relates to an odour control material comprising a water-insoluble particulate odour control agent. The invention also relates to a method for the preparation of the odour control material. The present invention further relates to an absorbent product comprising the odour control material.

BACKGROUND OF THE INVENTION

Odour prevention in connection with the use of absorbent products, such as incontinence and/or feminine products is an important comfort factor for consumers. Bodily fluids, such as blood and urine, are collected and stored in absorbent products and odours may easily arise. It is important for the wearer that these odours do not spread into the environment and the wearer needs to feel safe when using absorbent products both in respect of leakage and odour prevention or control.

In the field of absorbent products, several different solutions are used to prevent odours. For example, odours can be masked by the use of perfumes or deodorizing compounds. Odours may also be adsorbed or absorbed to particles having a large surface area, such as activated carbon, zeolite and starch-based particulate materials. Acidic and/or alkaline odours may be neutralized by the use of substances like baking soda and/or citric acid. For bacteria inhibition, substances having low pH or metal salts can be used. Accordingly, different odour control agents may be used to prevent odours in different manners.

Odour control agents in particulate form, such as the above-mentioned activated carbon, zeolite and starch-based materials, have been proved to have excellent odour-adsorbing characteristics due to the large surface area of the particles. However, there are some drawbacks related to the use of such particulate odour control agents, which may be in a powder form: for example, such powders are very difficult to handle in dry processes due to dusting problems. Powders may contaminate both process equipment and products. The powder may be spread in the working environment and in the worst case contaminate the working environment and/or cause dust explosions.

Further, problems with appearance of white absorbent products may arise if the powder, for example activated carbon powder, dusts during the manufacture of the products. The activated carbon may be spread in the products also outside the desired positions and therefore deteriorate the appearance of the products. It is desirable to keep the products clean outside the areas where the odour control agent is aimed to be positioned.

Particulate odour control agent powders may also be difficult to disperse in an even manner in the absorbent products. For example, humidity of the atmosphere may cause the particulate material to build lumps, and this may cause an uneven distribution in the production process and consequently in final products. Further, since particulate odour control agents adsorb odorous substances from the ambient air, there is a risk that the adsorption capacity of the particles decreases under storage.

In the prior art, there have been attempts to decrease dusting problems of powders as for example disclosed by EP0392528, in which a particulate odour control agent is bound to a fibrous base web, such as non-woven or paper web. The porous base web is dipped in a saturant slurry containing the odour-absorbing particulate and a binding agent, together with a surfactant. The excess slurry is then squeezed from the web and the web is dried. According to EP0392528, it is essential that the particulate material is effectively bound to the base web. Accordingly, a base web is needed to carry the odour-absorbing particles and the web as a whole is used in a final product. Therefore, possibility to use this web material is limited to products where the base web is needed as a part of the end product. This may complicate the production process and result to an expensive final product. Also, since the odour-absorbing particulate material is bound to the fibre web, the whole surface area of the odour-absorbing material is not used for absorption of odours. Further, the odour-absorbing material is exposed to the surrounding environment, whereby the odour-absorbing properties of the particulate material may be impaired during storage.

Thus, there is still a need to improve handleability of particulate odour control agents while good odour adsorbing/absorbing properties are maintained or improved, especially after storage.

SUMMARY OF THE INVENTION

It is an object of the present invention to improve handleability of particulate odour control agents in production processes. It is a further object of the present invention to improve the distribution of the particulate odour control agents so that an even distribution in the final products can be obtained. It is also an object of the present invention to maintain the adsorption capacity of the particulate odour control agent during storage. To improve adsorption of odours, it would be desirable to be able to use the whole surface area of the particulate odour control agent for odour adsorption.

The objects above are achieved by the present odour control material consisting of a water-insoluble particulate odour control agent and a thermoplastic water-soluble carrier matrix encapsulating the odour control agent. The carrier matrix dissolves when in contact with an aqueous solution, such as urine. The odour control material is obtained by means of thermoforming, e.g. by means of extrusion, and the particulate odour control agent is encapsulated in the carrier matrix, thereby minimizing the dusting problems experienced in connection with the use of particulate odour control agents. Since the carrier matrix dissolves when it contacts aqueous liquids, the odour control agent is released and an effective odour reducing can be obtained.

The odour control material may be obtained by means of extrusion. Extrusion is a well known and relatively simple and cost-effective way of forming materials from thermoplastic raw materials. Different forms and shapes of products can be easily obtained by extrusion.

The particulate odour control agent is preferably activated carbon, zeolite or a starch based particulate odour control agent. These odour control agents are very effective in odour adsorbing and/or absorbing. Especially, activated carbon has excellent odour-adsorbing properties.

The thermoplastic water-soluble carrier matrix comprises a water-soluble polymer which may be polyethylene oxide, polyvinyl alcohol, polysaccharide such as modified starches or sugars or sugar alcohols, polyacrylamide, polyvinylamine, polyvinylpyridine and polyvinylpyrrolidine, or a mixture thereof. These polymers are easy to process, and are non-toxic, whereby they are suitable for use in hygienic products. The water-soluble carrier matrix may also comprise additives such as plastisizer, stabilizer, agent improving dispersibility, pH regulating agent or antimicrobial substances, whereby different properties may be provided to the odour control material, odour reducing effect may be further improved and/or processability of the carrier matrix material can be improved.

The weight ratio carrier matrix to odour control agent is from 1:10 to 10:1. It is desirable to include a large amount of odour control agent in the material.

The odour control material is in the form of a film, fibres or filaments, or a fibre web. All these may be readily used in for example absorbent products, and thus minimal changes in the existing manufacturing processes are needed.

The odour control material may be in the form of a film and may have a thickness of 10 to 2000 micrometers. The film may be crushed into flakes or used as such. The odour control material may also be in the form of fibres, such as staple fibres and have a fibre length of from 1 to 40 mm and linear mass density of from 1.7 to about 10.000 dtex. Fibres may be used as complement to other fibres in the product and thus can be used in the existing manufacturing processes. Further, the odour control material may be a nonwoven fibre web, which can be used as such or as a part of a laminate fiber web usable in e.g. absorbent products.

The invention further relates to a method for preparation of the odour control material and comprises the steps of:
 i. providing a water-soluble thermoplastic carrier matrix material in a solid form;
 ii. providing a particulate odour control agent in a solid form;
 iii. blending the particulate odour control agent with the carrier matrix material to provide an even dispersion in which the particulate odour control agent is solid;
 iv. heating the carrier matrix material to a melting temperature of from about 70 to about 300° C. to at least partially melt the carrier matrix material wherein the particulate odour control agent remains solid;
 v. thermoforming the even dispersion to form a film, fibres or a fibre web;
 vi. cooling the thermoformed material;
 vii. collecting the formed material.

When the odour control material is a film the method may further comprise a step of punching the film to provide holes in the film and/or a step of crushing the obtained film to provide flakes. In this way, film products with different structure and solubility properties may be obtained since e.g. small flakes dissolve quicker to aqueous solutions than large volumes of film material.

When the odour control material obtained is in the form of staple fibres, the extrusion can be performed through a spinneret to provide fibres having a linear mass density of from 1.7 dtex to 10 000 dtex. The fibres may be used for example in different parts of an absorbent product to provide efficient odour control in desired positions.

When the odour control material is in the form of a fibre web, the method may further comprise a step of providing a fibre web being a meltblown material, spunbond material or a carded fibrous web. These nonwoven materials are well known in the art and the odour control material may be used as such or as a part of a laminate of different nonwoven materials.

The present invention further relates to an absorbent product, such as a diaper, sanitary napkin or an incontinence product, comprising a back sheet, being distal from the body of the wearer in use of the product, a top sheet being proximal to the body of the wearer in use of the product, and an absorbent structure located between the top sheet and the backsheet, wherein the product comprises the odour control material of the present invention. The absorbent product may comprise a further layer, the layer being the odour control material of the present invention. In this way, the layer may be easily incorporated to an absorbent product to provide efficient odour control. The odour control material may be comprised as fibres or flakes in the absorbent product and the fibres or flakes may be comprised in the absorbent core of the absorbent product. In this way, the odour control material will come into contact with liquid and thus, the odour control agent is released from the carrier matrix and thus efficient odour control can be provided.

These and other objects and advantages of the present invention are described more in detail in the following detailed description and claims.

DETAILED DESCRIPTION

Definitions

By odour control agent is meant a substance which is able to adsorb or absorb odorous substances.

By water-insoluble is meant a substance which does not dissolve in water or aqueous solutions.

By particulate is meant solid substances consisting of fine separate particles.

By thermoplastic is meant that a material becomes mouldable or soft when heated and that it returns to a solid state when cooled without any essential changes in material properties.

By carrier matrix is meant a substance or material which carries and/or encloses a particulate material.

By water-soluble is meant a substance which is capable of dissolving when in contact with water or an aqueous solution, e.g. urine or blood. In this context it is further meant that the water-soluble material dissolves at least partially so that water-insoluble particles enclosed in a water-soluble carrier matrix are released from the carrier matrix.

By thermoforming is meant a process in which a thermoplastic material is heated to a forming temperature, in which the thermoplastic material is at least partially melted so that it is formable and then a specific product, such as a film, fibres or filaments or a fibre web, is formed and cooled.

By extrusion is meant thermoforming in which a product is continuously formed of a mouldable or extrudable material, such as a thermoplastic material, by passage through a die of a desired cross-section.

By hydrophobic material is meant a material which, when measured on a flat surface, when in contact with a water droplet has a contact angle water droplet to surface of equal or larger than 90°.

By hydrophilic material is meant a material which, when measured on a flat surface, when in contact with a water droplet has a contact angle water droplet to surface of less than 90°.

The odour control material according to the present invention consists of a water-insoluble particulate odour control agent and a thermoplastic water-soluble carrier matrix for the odour control agent. Different components of the odour-control material according to the present invention are described in detail in the following description.

Odour Control Agent

The odour control agent of the present invention is particulate and water-insoluble. Any such odour control agent may be used, and suitable odour control agents for use in the odour control material according to the present invention include hydrophobic odour control materials in powder form, such as activated carbon. Also zeolites, which can be natural zeolites and synthetic zeolites, such as for example aluminosilicate molecular sieve powders, and starches and starch-based particulate agents such as different types of chitin derivatives, certain alginates, amylose, such as V-amylose are useable as odour control agents in the present invention. Further, the odour control agent may include clays such as bentonite, cellulose-based structures with large specific surface area and diatomaceous earth. Also, the odour control agent may be polymeric resin materials, ion exchange resins and polystyrene derivates. Also, certain metal oxide powders may be usable as odour control agent. The odour control agent may also be a mixture of two or more water-insoluble particulate odour control agents.

The particles of the odour control agent may have a particle size of from about 0.1-1000 μm and is preferably from about 1 μm to about 250 μm, measured according to ASTM D5158. Particles having a size smaller than 0.1 μm are often difficult to handle. On the other hand, particles which are larger than 250 μm may feel uncomfortable or uneven in final products where the odour control agent is used, e.g. in absorbent products. Therefore, the particles should be sufficiently fine or small so that they do not cause for example skin irritation.

The specific surface area of the particles determines the area or the substance that is available for binding of and/or interaction with other substances, or the total surface area of the particles in a gram of the substance. The specific surface area in this context is defined as BET-surface area. The BET-theory describes the adsorption of gas molecules to a solid surface and is based upon an assumption for the energy for the adsorption of the first layer. By measuring the volume of the nitrogen gas after desorption the specific surface area is calculated. The method has been developed by Brunauer, Emmett and Teller (BET). The skilled person would know conventional instruments for performing the measurement.

Generally, the BET-specific surface area of the water-insoluble particulate odour control agent used in the present invention may be from about 5 $m^2/g$ to about 1500 $m^2/g$ and is preferably larger than about 100 $m^2/g$ and preferably of at least 500 $m^2/g$. The specific surface area depends on the physical properties of the product. E.g. the BET specific surface area of starch-based particulate agent may be from about 5 $m^2/g$-500 $m^2/g$. On the other hand, in the market today existing powdered activated carbon (PAC) products may have a surface area of up to 1500 $m^2/g$. The larger the specific surface area of the particles is, the better the odour adsorbing property is.

The particulate and water-insoluble odour control agent may be hydrophobic, whereby the odour control agent particles may adsorb hydrophobic odorous substances while aqueous solutions, such as urine, will pass the particles without absorption. However, in some embodiments, the particulate odour control agent may also be hydrophilic or have both hydrophobic and/or hydrophilic properties. An example of such odour control agent is V-amylose.

The odour control agent in the present odour control material is preferably activated carbon, which is also called activated charcoal, activated coal or carbo activates, since activated carbon is very efficient as an odour control agent. Activated carbon is a form of carbon which has been processed to make it porous and it thus has a very large surface area which is available for adsorption of odours. Activated carbon can be made in particulate form as powders or fine granules.

The Carrier Matrix

The carrier matrix is water-soluble and comprises one or more water-soluble thermoplastic materials. It may also comprise water-soluble additives and/or other substances.

The carrier matrix preferably comprises at least one water-soluble thermoplastic polymer and may be a mixture of two or more water-soluble polymers. Different water-soluble polymers can have an influence on different process parameters, and may e.g. provide balanced water-solubility, melt processability, mechanical properties and/or physical properties.

The water-soluble carrier matrix dissolves when it comes to contact with aqueous solutions so that water-insoluble particles enclosed in the water-soluble carrier matrix are released from the carrier matrix. The carrier matrix dissolves at least partly to enable that the particulate, water-insoluble odour control agent (also referred to as particles) can come into contact with odorous substances. Preferably, the water-soluble material dissolves completely in water or the aqueous solution.

Suitable water-soluble polymers may contain a hydrophilic functional group or groups which render the polymer water-soluble. The functional group may be e.g. a hydroxyl group. Suitable water-soluble polymers may be for example polyethyleneoxide, polyvinylalcohol, polysaccharides, polyacrylamide, polyvinylamine, polyvinylpyridine and polyvinylpyrrolidine.

Polyethylene oxides (PEO), which can be formed of ethylene oxide monomers and derivatives thereof, have a molecular weight of from about 50,000 to about 1,000,000 g/mol, and is preferably between 100,000-600,000 (g/mol). If the molecular weight is lower, the polymer becomes very brittle. However, also brittle polymers are usable in some embodiments of the present invention. If the molecular weight is higher, the polymer may become difficult to dissolve in aqueous solutions. Polyethylene oxides have an advantage of being non-toxic, stable to heat, they are inert to many chemical agents and they do not hydrolyze or deteriorate.

Polyvinyl alcohol is easy to use in film forming processes and is water-soluble. Suitable polyvinyl alcohol polymers may have a molecular weight of from about 3,500 to about 700,000 (g/mol).

Also polysaccharides may be used in the water-soluble carrier matrix of the present invention. Polysaccharides may be for example chemically modified starches which are soluble in water, such as dextrin. The starches may be derived for example from wheat, corn, waxy corn, sorghum, rice, and waxy rice; potato; roots, sweet potato and arrowroot. Examples include sugars containing one or more of glucose, sucrose, fructose, raffinose, maltodextrose, galactose, xylose, maltose, lactose, mannose, and erythrose, sugar alcohols such as e.g., erythritol, xylitol, malitol, mannitol, and sorbitol, polyols e.g., ethylene glycol, glycerol, propylene glycol, dipropylene glycol, butylene glycol, and hexane triol, etc.

Starches may have a molecular weight ranging from about 3,000-1,000,000 grams per mole (g/mol), preferably from about 3,000-5,000 g/mole.

Also other polymers may be used, such as polyacrylamide which can be formed of acrylamide monomers and derivatives thereof, polyvinylamine, polyvinylpyridine which can be formed of vinyl pyridine monomer and polyvinylpyrrolidine, which can be formed monomers such as vinyl pyrrolidone monomer.

The carrier matrix may also include water-soluble additives, such as plastisizers, stabilizers, agents improving dispersibility, pH regulating agents or antimicrobial substances. Additives may influence processability of the carrier matrix material or may provide the material with enhanced odour-control properties, e.g. if the pH of the carrier matrix can be lowered or if antimicrobial agents are added to the carrier matrix.

Odour Control Material and Preparation Thereof

The odour control material of the present invention is obtained by means of thermoforming, such as extrusion. The thermoplastic material of the carrier matrix is usually provided in solid form, for example as granules. The solid granules may be blended with a particulate odour control agent either before melting or after the melting or heating of the thermoplastic material to a thermoforming or extrusion temperature. The carrier matrix material and the particulate odour control agent are mixed to form an even dispersion before thermoforming and the dispersion can then be for example extruded to form a film, fibres or a fibre web, in which the particulate odour control agent is evenly distributed. In this way, it is possible to further process and/or use the odour control material in various products while the problem with dusting is minimized, since the particulate odour control agent is enclosed in the carrier matrix. When the carrier matrix comes into contact with aqueous solutions, such as urine, it dissolves, whereby the odour control agents, which are not water-soluble, are released from the web. In this way the odour control agents are encapsulated and protected by the carrier matrix until the odour control material contacts aqueous liquids. When the particles are released from the carrier matrix, the whole particle may act as odour adsorbing or absorbing agent and the total surface area of each odour control agent particle can be used for odour control.

In general, the particulate odour control agents are not meltable. However, if the particulate odour control agent is meltable, the melting point of the carrier matrix should be lower than the melting point of the particulate odour control agent, so that the odour control material can be formed by means of thermoforming, e.g. by means of extrusion. The melting point of the carrier matrix material may vary depending on the properties of the thermoplastic material chosen within the range of from 70° C. to about 300° C. For example, if the particulate odour control agent has a melting point of 300° C., the carrier matrix material could have a melting point below e.g. about 200° C., and the processing temperature should be kept below 300° C. Further, if the odour control agent is activated carbon, any water-soluble thermoplastic material could be used as a material for the carrier matrix, since the melting point of the activated carbon is above 3000° C. Accordingly, the particulate odour-control agent should not melt during thermoforming of the odour control material.

The weight ratio of odour control agent to water-soluble material may be from about 1:10 to 10:1. The particulate odour control agent may be present in an amount of from about 10 wt.-% to about 90 wt.-% of the total weight of the odour control material.

According to one aspect of the invention, the odour control material may be in the form of a film. The film may be obtained by means of extrusion, such as film casting, die extruding with a flat die and/or calendering, film blowing, etc. or any other suitable extrusion method as is well known in the art. In all the methods, the thermoplastic carrier matrix material is melted and blended with the particulate odour control agent, and the heated mixture is then extruded through a die to form a film. Calendering may be included to provide a smooth or a textured surface for the film.

For example, the cast film process involves the extrusion of molten polymers through a flat die to form a thin film. This film is "pinned" to the surface of a chill roll with an air knife or vacuum box. The process starts with the feeding of plastic resins by means of a gravimetric feeding system to one or more extruders. The materials are melted and mixed by the extruders, filtered and fed to the die system. The molten polymer travels through a flat die system to adopt its final flat film shape. Immediately after exiting the die, the molten curtain enters the cooling unit where its temperature is lowered with a water cooled chill roll to freeze the film. The die system is formed by the die and feedblock (if the process requires coextrusion) or simply the die, if the process is that of mono-layer extrusion. Cast film production is well known for the man skilled in the art of converting polymers into films.

Further, calendering is a process where a large amount of molten plastic is placed between rollers and rolled to turn it into sheets. The rollers are hot and keep the plastic in its semi-molten state allowing it to be rolled thinner and thinner as it passes through rollers which are closer and closer together. When it is at the required thickness it is rolled through cold rollers to enable it to go hard and is then wound into rolls. Calendering process is a well know process used for example for PVC.

Accordingly, the method for the preparation of the film comprises mixing the particulate odour control material with the water-soluble carrier matrix material in an extruder and by blending the materials in a melting section of the extruder in which the carrier matrix material is brought into a molten or semi-molten state. The material is then extruded through for example a flat die to form a film. The film may have a thickness of about 10-2000 μm.

The odour control material in the form of a film may be treated before it is collected or rolled up. The film may be punched or calendered to make the surface of the film uneven. The holes or irregularities in the film may improve the ability of the carrier matrix to dissolve in aqueous solutions, and may also improve processability of the material. The material can then be rolled up or cut into sheets of desired size and used as such. The film material may also be "crushed" or cut into small pieces or flakes. The flakes can be blended with another material, e.g. fluff pulp, which absorbs liquids. If the film is crushed into small pieces, a further advantage is obtained since also brittle polymers, such as polyethylene oxide may be used to form the film, since there is no requirement for a high tensile strength. To provide the odour control material in the form of a film material has many advantages. The film is easy to prepare, it can be treated in many ways to provide different kinds of surface textures, the film can be collected and shipped to further production of final products in an easy way.

According to another aspect of the invention, the odour control material is in the form of a fiber web. The odour control material is extruded to form a fiber web. The formed fiber web may be a meltblown fiber web, spunbond fiber web or carded fiber web that are all conventional fiber webs well known in the art. A meltblown fiber web is basically prepared by melting thermoplastic materials and then by using high-velocity air or another appropriate force to attenuate the filaments. The filaments are gathered onto a conveyor or takeup screen to form a fine fibrous and self-bonding web. A carded fiber web is basically formed after extrusion of fibres in a card which aligns fibers in the machine direction whereafter the web is bonded. A spun-bonded web is basically prepared by depositing extruded, spun filaments onto a collecting belt in a uniform random manner followed by bonding the fibers. There are many advantages with the fiber web form. The fiber web produced may be used as such or it may be a part of a laminate included in the final product, e.g. an absorbent product. The fiber web is easy to process in further manufacturing steps and also the fiber web may become an integrated part of the product According to a further aspect of the invention, the odour control material may be in the form of fibres, i.e. filaments or staple fibers having a length of about 1 to 40 mm and a linear mass density of 1.7 dtex-10,000 dtex. Preferably, the fibres are staple fibres and have a length of from 3-40 mm and a linear mass density of from 10 dtex-2,000 dtex. However, depending on the solubility of the water-soluble thermoplastic material to aqueous solution, the linear mass density of the fibres may vary. The thinner the fibre is, i.e. the lower the value for the linear mass density, the quicker the water-soluble substances in the fibres dissolve. The fibres are formed by means of extrusion. In the manufacturing method, fibers are created by forcing a viscous liquid including the melted thermoplastic material and particulate odour control agent, through a spinneret to form filaments or fibers of desired length. The fibers are cooled and collected into bales. These bales can then be used in the production of e.g. absorbent products and spread to the absorbent core in a uniform manner. It is an advantage of the fibres that they may be blended with other fibres used in a product, e.g. in an absorbent product.

Absorbent Product

The odour control material may be used in an absorbent product. The absorbent product may have the following structure. Starting from the side closest to the wearer is a top sheet which may be for example a nonwoven fabric. Beneath the top sheet an optional liquid distribution layer, an acquisition layer, can be positioned. Beneath the liquid distribution layer, or directly beneath the top sheet (in case no liquid distribution layer is present) an absorbent core is positioned. For example, the absorbent core may be a pressure-bonded airlaid core comprising superabsorbent polymers. Beneath the core structure, a back sheet is provided. The back sheet may be for example a plastic film. At the outside of the back sheet, adhesive or glue strings may be provided to make it easier to fasten the absorbent product during use. A release paper is then positioned to protect the glue strings. An edge sealing, binding optional textile edges, a liquid distribution layer and a back sheet at the longitudinal edges can also be provided. The edge sealing may also be used to seal only the top layer and the backsheet, which thereby encapsulate the other layers, such as absorbent core, in between the top layer and backsheet. The odour control material of the present invention may be present inside and in proximity of any of the layers of an absorbent product, or it may be spread on top of any of the layer or it can be mixed with the fibres of the absorbent core. Examples of different embodiments are shown in the accompanied FIGS. 1-9.

The absorbent product can be divided into different zones as for example defined in WO2007067111. Generally, the product may have (a) a wet zone, which is intended to store liquid during use. The wet zone comprises an absorbent structure or absorbent core. The product further has (b) a dry zone, which is intended to be substantially dry during use. The dry zone can be defined by outer edges, belt, elastics, backing sheet, wings and optionally outer parts of the standing gathers, and (c) an interfacing zone adjoining the wet zone, which is defined by the part(s) of the top sheet receiving liquid, optionally the inner part of standing gathers, optionally an acquisition layer, and other parts adjoining the wet zone thereby occasionally being wet. The odour control material of the present invention may be placed in any zone of the absorbent product. Preferably, the odour control material is placed such that it comes into contact with fluids, i.e. in the wet zone and/or in the interfacing zone.

As mentioned above, the particulate odour control agents may be hydrophobic. Hydrophobic particles just added to an absorbent core may impair the liquid distribution as the surfaces of such particles are hard to wet. This problem can be reduced by the present invention as the hydrophobic particles are surrounded by a hydrophilic wettable carrier matrix material.

As mentioned above, the odour control material of the present invention may be placed anywhere in an absorbent product. However, the odour control material is preferably placed in the product such that it comes into contact with liquid, for example urine. If the odour control material comprises a carrier matrix which has a high solubility in an aqueous liquid, the odour control material will dissolve also when it comes to contact with a small amount of liquid, such as body sweat.

The odour control material may also be incorporated in the absorbent core. The absorbent core may be built up of one or more layers of defibrillated cellulose fibres, for example cellulose fluff pulp. The core may include also other materials, such as nonwoven material, foam material or synthetic fibre material. The core may also comprise superabsorbent material, such as superabsorbent polymer (SAP), which can bind fluid several times the weight of the superabsorbent material and forms a fluid-containing gel. The core may also comprise other components such as binders, form-stabilising components etc.

The pulp in the absorbent core may be chemically or physically treated in order to change the absorption properties. The absorbent layers may have compressed regions and/or may be compressed in the entire layer(s). It is also possible to enclose the absorbent layer(s) in an envelope of for example tissue material. In the prior art, it has been common to use tissue material in the absorbent core or in e.g. distribution layers.

The absorbent core may comprise more than one layer, e.g. three sub-layers. The sub-layers primarily comprise pulp. The odour control material of the present invention may be comprised in the first sub-layer, viewed from the wearer-facing side of the core, the second sub-layer and/or in the third sub-layer. However, the odour control material of the present invention is preferably positioned above or in the first sub-layer and on top of the layer comprising the superabsorbent polymer, so that it can be assured that a sufficient amount of liquid comes into contact with the odour control material so that the carrier matrix is dissolved. The odour control material incorporated in the core may be in the form of short staple fibres or film flakes. The film pieces and/or the fibres can be mixed with the cellulose fluff pulp used for the core material.

SHORT DESCRIPTION OF FIGURES

Examples of different embodiments according to the present invention are further illustrated in the accompanying Figures in which.

Figure 1:
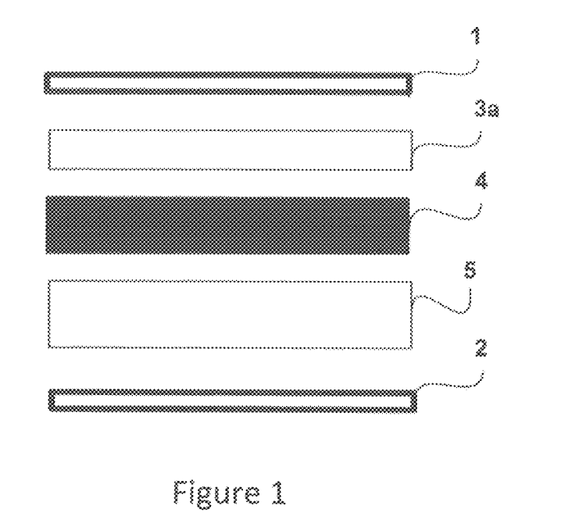
FIG. 1 shows schematically layers of an absorbent product comprising the odour control material of the present invention in form of a film.

FIG. 1 shows an example of layers of an absorbent product, in which one of the layers is the odour control material of the present invention. The product comprises a surface or top layer 1 of nonwoven material and a liquid impervious backing material layer 2. In between the top layer 1 and the backing layer 2, below the top layer 1, an acquisition material layer 3a is provided to enhance the liquid distribution in the product. An odour control material in the form of a film 4 according to the present invention is provided below the acquisition layer 3a and on top of an absorbent core 5. The film 4 has a smooth surface and is not punched. The film 4 may come into contact with liquid, such as urine, and thus, the carrier matrix is dissolved and the particulate odour control agent is released. Thereby, an effective odour control may be achieved and odours can be prevented from arising.

Figure 2:
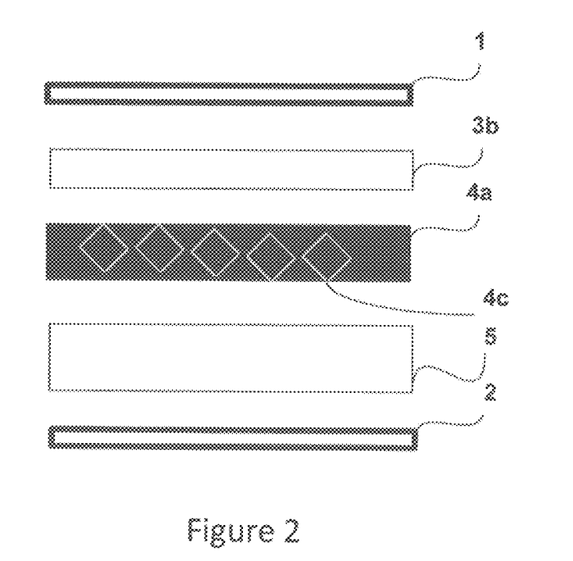
FIG. 2 shows schematically layers of an absorbent product comprising the odour control material of the present invention in form of a punched film.

FIG. 2 shows another embodiment of the present invention similar to the one of FIG. 1 but in which the film material layer 4a is punched. Also flakes 4c of the film may be present in this layer. The other layers of the product are a top layer 1 of nonwoven material, absorbent core 5 and a backing material layer 2. Below the top layer 1, an acquisition material layer 3b is provided.

Figure 3:
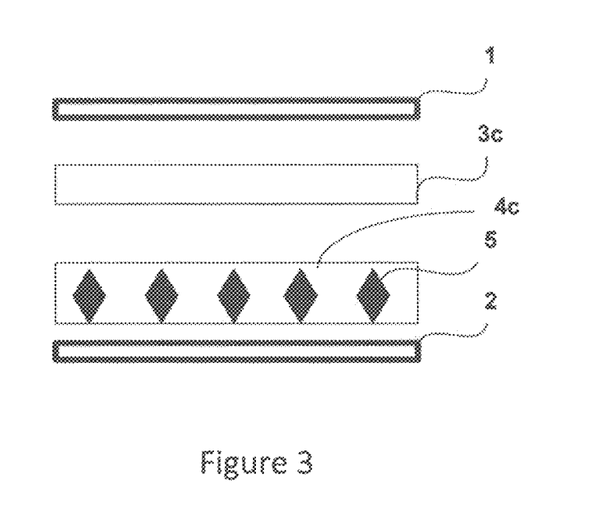
FIG. 3 shows schematically layers of an absorbent product comprising the odour control material of the present invention in form of film flakes.

FIG. 3 shows a further embodiment of the present invention in which a top layer 1 of nonwoven material and a backing material layer 2 are provided. Below the top layer 1, an acquisition material layer 3c is provided. Flakes 4c of a film material according to the present invention are added to an absorbent core 5 of the absorbent product. In this embodiment, also brittle water-soluble carrier matrix materials may be used.

Figure 4:
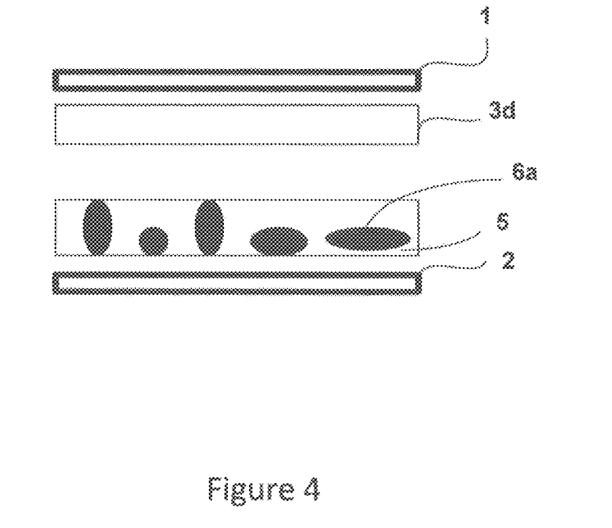
FIG. 4 shows schematically layers of an absorbent product comprising the odour control material of the present invention in form of fibres in a core.

FIG. 4 shows a further embodiment, in which the odour control material of the present invention is provided in the form of fibres 6a. Also in this embodiment, a top layer 1 of a nonwoven material and a backing material layer 2 are provided. Below the top layer 1, an acquisition material layer 3d is provided. Odour control material fibres 6a are blended with fibres of an absorbent core 5. In this way the odour control material may be added to the absorbent product in one step, whereby the odour control material of the present invention may be used in an existing process in an easy way.

Figure 5:
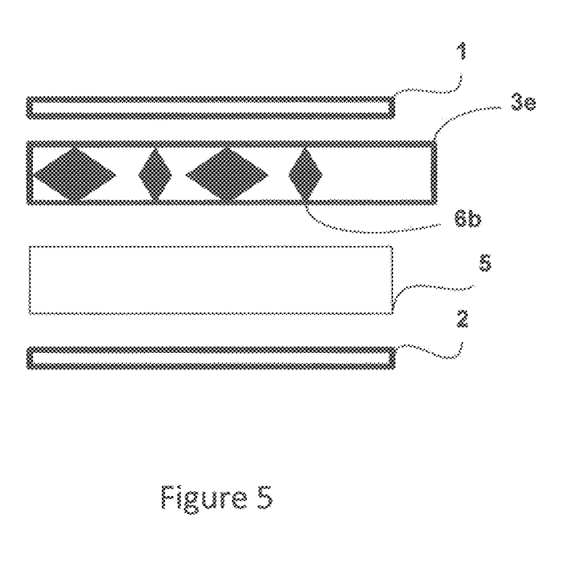
FIG. 5 shows schematically layers of an absorbent product comprising the odour control material of the present invention in form of fibres in an acquisition material.

Still another embodiment is shown in FIG. 5. Also, in this embodiment a top layer 1 of nonwoven material and a backing material layer 2 are provided. Below the top layer 1, an acquisition material layer 3e is provided, in which odour control material in the form of fibres 6b is mixed. Below the acquisition material, 3e, an absorbent core 5 is provided.

Figure 6:
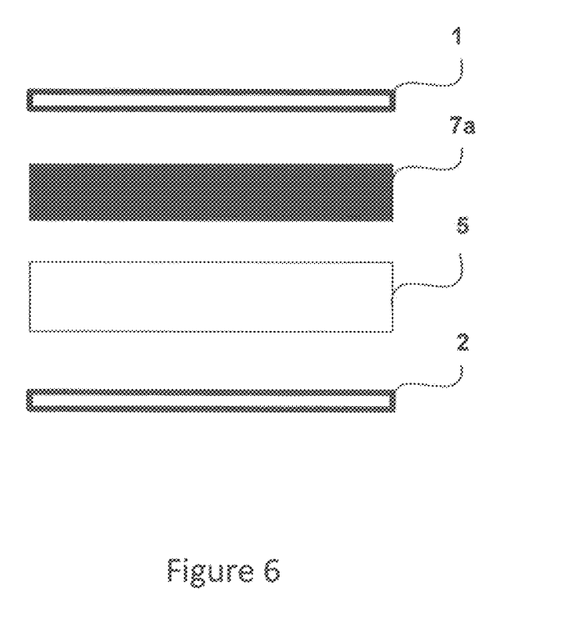
FIG. 6 shows schematically layers of an absorbent product comprising the odour control material of the present invention in form of a nonwoven web.

In FIG. 6 an embodiment is shown in which, as above, a top layer 1 of nonwoven material and a backing material layer 2 are provided. Below the top layer 1, odour control material in the form of a nonwoven 7a according to the present invention is provided. Below the nonwoven 7a an absorbent core 5 is provided. The odour control material is provided in the form of a nonwoven, which may be rolled up to a roll, is easy to use in existing processes and is easily adapted to online manufacturing processes.

Figure 7:
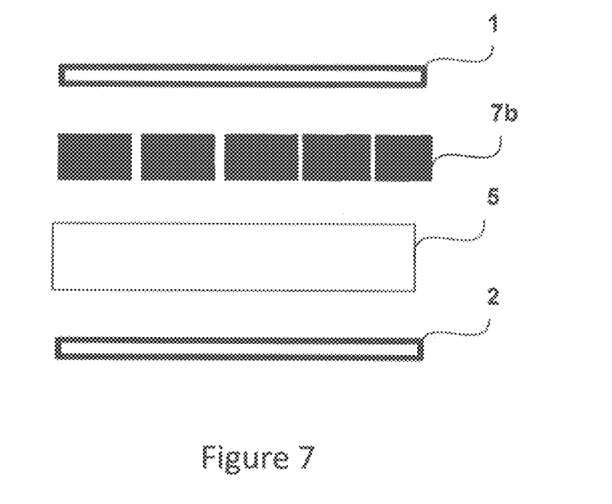
FIG. 7 and FIG. 8 show schematically layers of an absorbent product comprising the odour control material of the present invention in form of a punched nonwoven.
Figure 8:
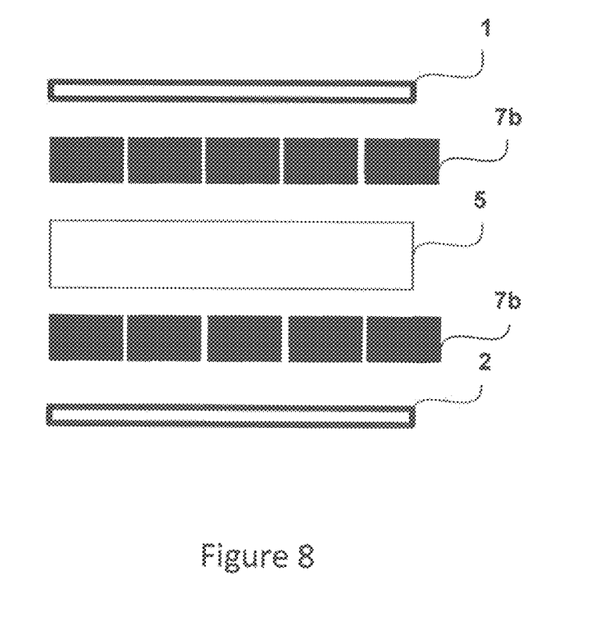
Figure 9:
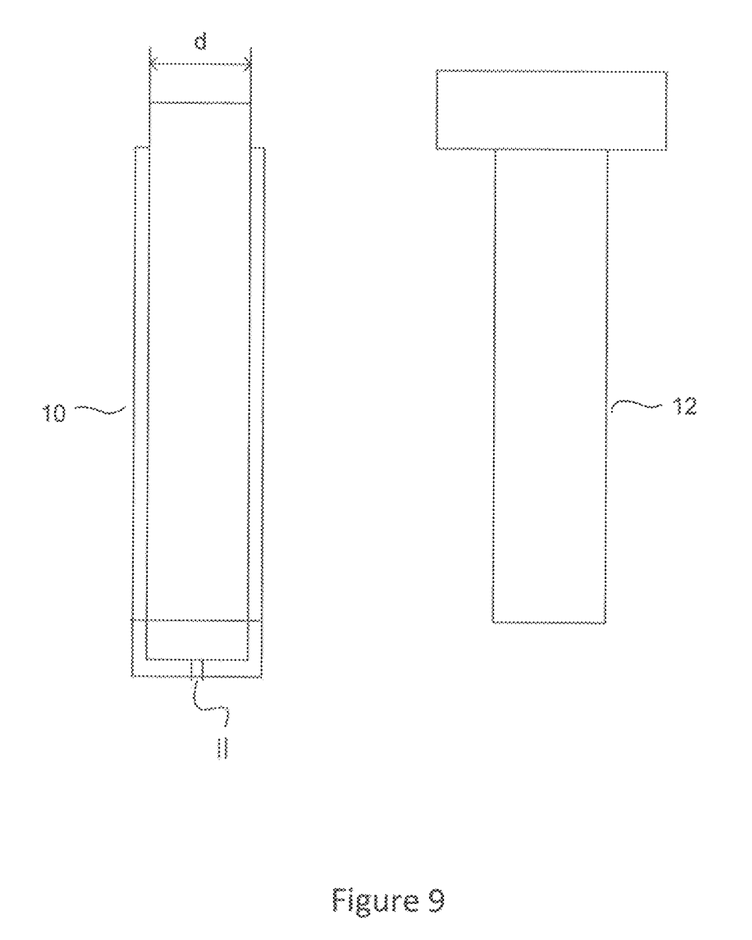
FIG. 9 shows schematically a test device used in Example 7.

In FIGS. 7 and 8, odour control material in the form of a punched nonwoven web 7b according to the present invention is provided. As above in connection with the embodiments shown in FIGS. 1-6, a top layer 1 of nonwoven material and a backing material layer 2 are provided. In FIG. 7, punched nonwoven is provided under the top layer 1. Below the punched nonwoven, an absorbent core 5 is provided. In FIG. 8, a further layer of nonwoven 7b is provided below an absorbent core and above the backing material layer 2. By providing punches in the nonwoven web, the water-solubility of the carrier material is further enhanced.

EXAMPLES

In the Examples below odour control material according to the present invention have been prepared. Molecular weight expressed in Daltons (Da) corresponds approximately to a molecular weight expressed in grams per mole.

Example 1

Preparation of an Odour Control Material According to the Present Invention in the Form of Odour-Reducing Flakes Containing 50 Weight-% Activated Carbon in Polyethylene Oxide with a Molecular Weight of 100,000 Da (Material A).

5 g of activated carbon powder, Norit SA2, delivered by Sigma-Aldrich, was mixed in a beaker with 5 g polyethylene oxide powder with a molecular weight of 100,000 Da, also purchased from Sigma Aldrich. The beaker was placed in an oven at 130° C. for about 1 hour in order to melt the polyethylene oxide. During this period the blending was manually mixed using a stainless steel spoon. The blending was then placed between two Teflon cloths and a pre-heated steel plate and a pre-heated steel cylinder, both with a temperature of about 130° C. were used to manually compress the material to a film. This was achieved by placing the Teflon cloths on the heated plate and rolling the cylinder several times over the clothes until the material between the cloths had been squeezed out to a film. The material was then cooled to room temperature and the Teflon cloths were then detached from the polyethylene oxide film with activated carbon particles. The film, which had an approximate thickness of 1 mm was then manually torn into flakes with the approximate area of 3 mm*3 mm.

Example 2

Preparation of an Odour Control Material According to the Present Invention in the Form of Odour-Reducing Flakes Containing 50 Weight-% Activated Carbon in Polyethylene Oxide with a Molecular Weight of 600,000 Da (Material B)

5 g of activated carbon powder, Norit SA2, delivered by Sigma-Aldrich, was mixed in a beaker with 5 g polyethylene oxide powder with a molecular weight of 600,000 Da, also purchased from Sigma Aldrich. The beaker was placed in an oven at 130° C. for about 1 hour in order to melt the polyethylene oxide. During this period the blending was manually mixed using a stainless steel spoon. The blending was then placed between two Teflon cloths and a pre-heated steel plate and a pre-heated steel cylinder, both with a temperature of about 130° C. were used to manually compress the material to a film. This was achieved by placing the Teflon cloths on the heated plate and rolling the cylinder several times over the clothes until the material between the cloths had been squeezed out to a film. The material was then cooled to room temperature and the Teflon cloths were then detached from the polyethylene oxide film with activated carbon particles. The film, which had an approximate thickness of 1 mm was then manually torn into flakes with the approximate area of 3 mm*3 mm.

Example 3

Preparation of an Odour Control Material According to the Present Invention in the Form of Odour-Reducing Flakes Containing 50 Weight-% Activated Carbon in a Mixture of Saccharose and Glucose (Material C).

3.86 g granulated sugar from the company Dansukker was placed in a beaker and added 1.14 g distilled water. The mixture was slowly heated on a heating plate until all sugar had melted. Then, 1.14 g glucose with the trade name Dextropur, bought from a local food shop, was added and the temperature of the heating plate was increased. When the temperature of the sugar had reached about 152° C., 5 g activated carbon powder, Norit SA2, delivered by Sigma-Aldrich, was manually mixed into the melted sugar by the aid of a spoon of stainless steel. The mixture was then placed between two Teflon cloths and kept in an oven at about 150° C. for about 5 minutes. The Teflon cloths, with the mixture of melted sugar and activated carbon were then placed on a preheated steel plate, with a temperature of 150° C. A pre-heated steel cylinder, with a temperature of about 150° C., was used to manually compress the material to a film. This was achieved by rolling the cylinder several times over the clothes until the material between the cloths had been squeezed out to a film. The material was then cooled to room temperature and the Teflon cloths were then detached from the sugar film with activated carbon particles. The film, which had an approximate thickness of 1 mm was then manually torn into flakes with the approximate area of 3 mm*3 mm.

Example 4

Preparation of an Odour Control Material According to the Present Invention in the Form of Odour-Reducing Flakes Containing 50 Weight-% Activated Carbon in Thermoplastic Starch (Material D)

2.14 g starch, Solcoat 55 from Solam AD, 2.14 g Urea, Sigma Aldrich, and 0.72 g Sorbitol, Sigma Aldrich, was added 10 a beaker. To this mixture 5 g distilled water and 5 g of activated carbon powder, Norit SA2, delivered by Sigma-Aldrich, were added. After thorough mixing, the beaker was placed in an oven with the temperature 150° C. At this temperature, the water first evaporates and then urea reacts with starch forming starch carbamate. This modified starch plasticized with sorbitol has thermoplastic properties. The blending was then placed between two Teflon cloths and a pre-heated steel plate and a pre-healed steel cylinder, both with a temperature of about 130° C. were used to manually compress the material to a film. This was achieved by placing the Teflon cloths on the heated plate and rolling the cylinder several times over the clothes until the material between the cloths had been squeezed out to a film. The material was then cooled to room temperature and the Teflon cloths were then detached from the thermoplastic starch film with activated carbon particles. The film, which had an approximate thickness of 1 mm was then manually torn into flakes with the approximate area of 3 mm*3 mm.

Comparative Example 5

Comparative Example of a Material not Included in the Invention. Preparation of Flakes Containing 50% Activated Carbon in Styrene-Acrylate Copolymer (Material E)

5 g of activated carbon powder, Norit SA2, delivered by Sigma-Aldrich, was mixed in a beaker with 10 g of a styrene-acrylate latex dispersion with the trade name Mowilith TA2250S from the company Celanese. The latex dispersion had a content of styrene-acrylate copolymer of 50% in water. After thorough mixing, the beaker was placed in an oven with a temperature of 150° C. for about 3 h in order to evaporate the water. The mixture of activated carbon in styrene-acrylate copolymer was then placed between two Teflon cloths and compressed to a film by the aid of a press with heated plates. A plate temperature of 150° C. was used and a mechanical load of 400 kN was applied on the material for about 1 minute. The material was then cooled to room temperature and the Teflon cloths were then detached from the styrene-acrylate copolymer film with activated carbon particles. The film, which had an approximate thickness of 1 mm was then manually torn into flakes with the approximate area of 3 mm*3 mm.

Example 6

Dissolution of the Polymer Carrier Matrix

This test was performed to investigate how much of the carrier matrix that was dissolved in one minute in a tempered saline solution.

Materials:

Saline solution, temperature 35-37° C.

Vortex apparatus IK MS2, speed 1500 rpm

Test tube 15 ml

Filter paper, 2 layers, Tork 23 g/m2

Funnel

Polymer carrier matrix, thickness 300-2000 μm, with 50 weight-% of activated carbon     Prov A Polyethylene oxide polymer 100,000 Da     Prov B Polyethylene oxide polymer 600,000 Da     Prov C Mixture of saccharose and glucose     Prov D Thermoplastic starch     Prov E Styrene-acrylate copolymer 0.02 g of the polymer carrier matrix with activated carbon was added to the test tube. Each material was in 1 to 3 pieces. Three ml of the tempered saline solution was poured into the test tube which was instantly placed on the Vortex. After 1 minute the content of the test tube was filtered. After filtration the filter paper was folded up and a visual assessment was made with respect to the proportion of the material which had been dissolved and/or softened and distributed on the filter paper.

TABLE 1

| Polymer carrier matrix | Dissolution % |
|---|---|
| Prov A | >90 |
| Prov B | >90 |
| Prov C | 100 |
| Prov D | 100 |
| Prov E | 0 |

Example 7

Preparation of an Odour-Reducing Thread Containing 50 Weight-% Activated Carbon in Polyethylene Oxide with a Molecular Weight of 600,000 Da 10 g of activated carbon powder, Norit SA2, delivered by Sigma-Aldrich, was mixed in a beaker with 10 g polyethyleneoxide powder with a molecular weight of 600,000 Da, also purchased from Sigma Aldrich. The beaker was placed in an oven at 130° C. for about 1 hour in order to melt the polyethylene oxide. During this period the blending was manually mixed using a stainless steel spoon. The blending was then transferred to a laboratory device, see FIG. 9, for extrusion of threads. This device consisted of a tube 10 in stainless steel with an inner diameter d of 18 mm and a length of about 150 mm. A nozzle with one hole 11 with the diameter 0.8 mm had been attached to one of the tube ends. A piston 12 with good fit was inserted into the tube. The extrusion device was then kept in an oven with the temperature 150° C. for about 1 hour. After heating, threads were prepared by pressing the piston into the tube by the aid of a workshop press. A thread of hot polyethylene oxide with particles of activated carbon was hereby extruded through the nozzle. The thread quickly became solid by the temperature reduction achieved by the cooling effect of the surrounding air. The length and weight of the thread were measured and its average fibre weight (linear mass density) was determined to about 9000 dtex.

Example 8

Measurement of Odour Reduction

Flakes prepared according to examples 1-4 were added to fluffed pulp and the ability or this mixture to reduce odours was determined by the following method.

The sample was placed in a 60 ml vial, after which 3.9 ml of 0.01 M phosphate buffered saline solution pH 7.4 from Sigma was added. Then 0.1 ml PEG300 with DMS (dimethyl sulfide), DMDS (dimethyl disulfide) and IVA (isovaleric aldehyde) were added so that the total amount of all three odour substances was 1000 ng/ml of each substance.

After 3 hours at 35° C. a SPME fiber (Supelco), 75 μm Carboxen-PDMS, was injected into the headspace above the sample and after an additional 0.5 hour the SPME fiber was analyzed with gas chromatography (GC), Thermo Finnigan Trace, with a MS detector. The peak area of each odour substance was determined for samples with treated pulp and the untreated reference pulp. The GC settings were:
Temperature program for GC: 30° C. (7 min); 3° C./min –70° C. (0 min), 40° C./min –250° C. (7 min).
Column: ZB-624 (Zebron), 30 m, 0.25 mm i.d. 1.40 μm film thickness
Inlet temperature: 250° C.
Transfer line: 220° C.
Mode; Splitless
MS: SIM (single ion monitoring). When DMS, IVA and DMDS were analyzed the following mass numbers were detected: 45, 46, 47, 57, 58, 61, 62, 79, 86 and 94.

The odour reduction is calculated for each odour substance from equation [1]

$$\text{Odour reduction} = (1 - A_1/A_0) \times 100\%$$

Where, $A_1$=Peak area of actual sample
$A_0$=peak area for sample with pure fluffed pulp To measure odour reduction according to the above-described method, a fluffed pulp was prepared by dry defibrillation of roll fluff pulp named IP RW Supersoft fluff pulp, produced by the company International Paper. Samples containing 1 g of this fluffed pulp were then prepared and their odour-reducing ability was determined. As a comparative sample, 1 g fluffed pulp was mixed with 0.3 g activated carbon powder, Noril SA2, delivered by Sigma-Aldrich. Samples 3-6 were prepared by mixing 1 g fluffed pulp with flakes according to the invention. As these flakes had an activated carbon content of 50 weight-%, 0.6 g was added to each sample. This means that samples 2-6 all contained 0.3 g activated carbon. All prepared samples are described in table 2.

TABLE 2

| Sample no | Content |
|---|---|
| 1 | 1 g fluffed pulp |
| 2 | 1 g fluffed pulp + 0.3 g activated carbon |
| 3 | 1 g fluffed pulp + 0.6 g flakes from example 1 |
| 4 | 1 g fluffed pulp + 0.6 g flakes from example 2 |
| 5 | 1 g fluffed pulp + 0.6 g flakes from example 3 |
| 6 | 1 g fluffed pulp + 0.6 g flakes from example 4 |

The odour-reducing ability of the samples described in table 2 was determined by analyzing the concentration of three relevant odorants, dimethylsulfide, dimethyldisulfide and isovaleric aldehyde, in the gas phase above the samples after injection of a test solution containing these compounds into vials with the different samples. The odour reduction is calculated by comparing the peak area of the actual sample with peak area of sample 1 according to equation [1]. The results from this investigation are shown in tables 3-5.

TABLE 3

Relative peak area from GC analysis and calculated reduction of dimethylsulfide

| Sample no. | Relative peak area | Calculated odour reduction |
|---|---|---|
| 1 | 1 | 0 |
| 2 | 0.059 | 94.1 |
| 3 | 0.087 | 91.3 |
| 4 | 0.056 | 94.4 |
| 5 | 0.047 | 95.3 |
| 6 | 0.014 | 98.6 |

TABLE 4

Relative peak area from GC analysis and calculated reduction of dimethyldisulfide

| Sample no. | Relative peak area | Calculated odour reduction |
|---|---|---|
| 1 | 1 | 0 |
| 2 | 0.001 | 99.9 |
| 3 | 0.008 | 99.2 |
| 4 | 0.004 | 99.6 |

TABLE 4-continued

Relative peak area from GC analysis and
calculated reduction of dimethyldisulfide

| Sample no. | Relative peak area | Calculated odour reduction |
|---|---|---|
| 5 | 0.002 | 99.8 |
| 6 | 0.001 | 99.9 |

TABLE 5

Relative peak area from GC analysis and calculated
reduction of isovaleric aldehyde

| Sample no. | Relative peak area | Calculated odour reduction |
|---|---|---|
| 1 | 1 | 0 |
| 2 | 0.007 | 99.3 |
| 3 | 0.023 | 97.7 |
| 4 | 0.010 | 99.0 |
| 5 | 0.005 | 99.5 |
| 6 | 0.002 | 99.8 |

As can be seen in tables 3-5, the odour reduction is high both for sample 2, which contains 0.3 g activated carbon and for samples 3-6, which each contain the same amount of activated carbon in odour control materials according to the invention. The examples show that the use of fine powder can be avoided without negative influence of the odour reduction.

The various aspects and embodiments of the invention can of course be modified within the scope of the invention. In order to further illustrate the invention, the following examples are provided, which however not should be interpreted as narrowing the intended scope of protection as defined by the appended claims.

The invention claimed is:

1. An odour control material consisting of a water-insoluble particulate odour control agent and a thermoplastic water-soluble carrier matrix encapsulating the odour control agent, wherein the carrier matrix dissolves when in contact with an aqueous solution, and wherein the odour control material is in the form of a film, fibres or filaments, or a fibre web, obtained by means of extrusion.

2. The odour control material according to claim 1, wherein the particulate odour control agent is activated carbon, zeolite or a starch based particulate odour control agent.

3. Odour control material according to claim 2, wherein the particulate odour control agent is activated carbon.

4. Odour control material according to claim 1, wherein the thermoplastic water-soluble carrier matrix comprises a water-soluble polymer selected from the group consisting of: polyethylene oxide, polyvinyl alcohol, polysaccharide, polyacrylamide, polyvinylamine, polyvinylpyridine, polyvinylpyrrolidine, and a mixture thereof.

5. Odour control material according to claim 1, wherein the water-soluble carrier matrix comprises an additive selected from the group consisting of: plastisizer, stabilizer, agent improving dispersibility, pH regulating agent, and antimicrobial substances.

6. Odour control material according to claim 1, wherein the weight ratio carrier matrix to odour control agent is from 1:10 to 10:1.

7. Odour control material according to claim 1, wherein the odour control material is in the form of a film and has a thickness of 10 to 2000 micrometers.

8. Odour control material according to claim 1, wherein the odour control material is in the form of fibres which are staple fibres and have a fibre length of from 1 to 40 mm and linear mass density of from 1.7 to about 10,000 dtex.

9. Odour control material according to claim 1, wherein the odour control material is a nonwoven fibre web.

10. Method for preparation of the odour control material according to claim 1, the method comprising the steps of:
  i. providing a water-soluble thermoplastic carrier matrix material in a solid form;
  ii. providing a particulate odour control agent in a solid form;
  iii. blending the particulate odour control agent with the carrier matrix material to provide an even dispersion in which the particulate odour control agent is solid;
  iv. heating the carrier matrix material to a melting temperature of from about 70 to about 300° C. to at least partially melt the carrier matrix material, wherein the particulate odour control agent remains solid;
  v. extruding the even dispersion to form a film, fibres or a fibre web;
  vi. cooling the extruded material;
  vii. collecting the formed material.

11. Method according to claim 10, wherein the odour control material obtained is a film.

12. Method according to claim 11, wherein the method further comprises a step of a step punching the film to provide holes in the film and/or a step of crushing the obtained film to provide flakes.

13. Method according to claim 10, wherein the odour control material obtained is in the form of staple fibres, wherein the extrusion is performed through a spinneret to provide fibres having a linear mass density of from 1.7 dtex to 10,000 dtex.

14. Method according to claim 13, wherein the method further comprises a step of providing a fibre web being a meltblown material, spunbond material or a carded fibrous web.

15. Absorbent product comprising a back sheet, being distal from the body of the wearer in use of the product, a top sheet being proximal to the body of the wearer in use of the product, and an absorbent structure located between the top sheet and the backsheet, wherein the product comprises the odour control material according to claim 1.

16. Absorbent product according to claim 15, wherein the absorbent product comprises a further layer, the layer being the odour control material.

17. Absorbent product according to claim 15, wherein the odour control material is comprised as fibres or flakes in the absorbent product.

18. Absorbent product according to claim 17, wherein the fibres or flakes are comprised in an absorbent core of the absorbent product.

19. Odour control material according to claim 1, wherein the aqueous solution is urine.

* * * * *